(12) United States Patent
Brannan

(10) Patent No.: US 8,334,812 B2
(45) Date of Patent: Dec. 18, 2012

(54) MICROWAVE ABLATION ANTENNA RADIATION DETECTOR

(75) Inventor: Joseph D. Brannan, Erie, CO (US)

(73) Assignee: Vivant Medical, Inc., Boulder, CO (US)

( * ) Notice: Subject to any disclaimer, the term of this patent is extended or adjusted under 35 U.S.C. 154(b) by 686 days.

(21) Appl. No.: 12/542,785

(22) Filed: Aug. 18, 2009

(65) Prior Publication Data

US 2010/0321257 A1 Dec. 23, 2010

Related U.S. Application Data

(63) Continuation-in-part of application No. 12/487,917, filed on Jun. 19, 2009.

(51) Int. Cl.
*G01R 29/10* (2006.01)
(52) U.S. Cl. ............ 343/703; 340/600; 600/430; 606/33
(58) Field of Classification Search .................. 343/703, 343/841; 340/573.1, 600; 600/430; 606/33
See application file for complete search history.

(56) References Cited

U.S. PATENT DOCUMENTS

| | | | |
|---|---|---|---|
| 4,215,275 A | 7/1980 | Wickersheim | |
| 4,448,547 A | 5/1984 | Wickersheim | |
| 4,560,286 A | 12/1985 | Wickersheim | |
| 4,580,557 A | 4/1986 | Hertzmann | |
| 4,753,248 A | 6/1988 | Engler et al. | |
| 5,375,596 A * | 12/1994 | Twiss et al. | 600/424 |
| 5,671,133 A | 9/1997 | Fujita | |
| 6,222,193 B1 | 4/2001 | Thurston et al. | |
| 6,424,869 B1 | 7/2002 | Carr | |
| 7,025,765 B2 | 4/2006 | Balbierz et al. | |
| 7,197,356 B2 * | 3/2007 | Carr | 600/430 |
| 2002/0075189 A1 | 6/2002 | Carillo | |
| 2002/0087079 A1 | 7/2002 | Kaufman et al. | |
| 2007/0191825 A1 | 8/2007 | Cronin et al. | |
| 2010/0145328 A1 * | 6/2010 | Hancock et al. | 606/33 |
| 2010/0286686 A1 * | 11/2010 | Hancock | 606/33 |

FOREIGN PATENT DOCUMENTS

| | | |
|---|---|---|
| DE | 390937 | 3/1924 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |

(Continued)

OTHER PUBLICATIONS

U.S. Appl. No. 08/483,742, filed Jun. 7, 1995.

(Continued)

*Primary Examiner* — Tho G Phan

(57) ABSTRACT

A radiation detector is disclosed. The radiation detector is disposed on a microwave antenna assembly. The radiation detector includes a receiving antenna adapted to receive microwave energy. The receiving antenna includes a first tubular antenna member and a second tubular antenna member disposed concentrically about a longitudinal axis defined by the microwave antenna assembly. The detector also includes at least one rectifier coupled to the receiving antenna adapted to rectify at least a portion of the microwave energy and a filter coupled to the at least one rectifier and adapted to convert the rectified microwave energy into a detection signal.

21 Claims, 4 Drawing Sheets

FOREIGN PATENT DOCUMENTS

| | | |
|---|---|---|
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0648515 | 4/1995 |
| EP | 0 836 868 | 4/1998 |
| EP | 1 159 926 | 5/2001 |
| EP | 1524719 | 4/2005 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO99/25248 | 5/1999 |
| WO | WO99/58065 | 11/1999 |
| WO | WO 2008/002517 | 1/2008 |

OTHER PUBLICATIONS

U.S. Appl. No. 08/136,098, filed Oct. 14, 1993.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/508,700, filed Jul. 24, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,462, filed Nov. 16, 2009.
U.S. Appl. No. 12/620,289, filed Nov. 17, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier. United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.

Anonymous. (1987) Homer Mammalok™ Breast Lesion Needle/Wire Localizer, Namic® Angiographic Systems Division, Glens Falls, New York, (Hospital products price list), 4 pages.

Anonymous. (1999) MIBB Site Marker, United States Surgical (Sales brochure), 4 pages.

Anonymous. Blunt Tubes with Finished Ends. Pointed Cannula, Popper & Sons Biomedical Instrument Division, (Products Price List), one page, Jul. 19, 2000.

Anonymous. Ground Cannulae, ISPG, New Milford, CT, (Advertisement) one page, Jul. 19, 2000.

B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.

B. Levy M.D. et al., "Update on Hysterectomy New Technologies and Techniques" OBG Management, Feb. 2003.

B. Levy M.D., "Use of a New Vessel Ligation Device During Vaginal Hysterectomy" FIGO 2000, Washington, D.C.

B. F. Mullan et al., (May 1999) "Lung Nodules: Improved Wire for CT-Guided Localization," Radiology 211:561-565.

B. T. Heniford M.D. et al., "Initial Research and Clinical Results with an Electrothermal Bipolar Vessel Sealer" Oct. 1999.

Bergdahl et al., "Studies on Coagulation and the Development of an Automatic Computerized Bipolar Coagulator" Journal of Neurosurgery 75:1 (Jul. 1991), pp. 148-151.

Bulletin of the American Physical Society, vol. 47, No. 5, Aug. 2002, p. 41.

C. F. Gottlieb et al., "Interstitial Microwave Hyperthermia Applicators having Submillimetre Diameters", Int. J. Hyperthermia, vol. 6, No. 3, pp. 707-714, 1990.

C. H. Durney et al., "Antennas for Medical Applications", Antenna Handbook: Theory Application and Design. p. 24-40, Van Nostrand Reinhold, 1988 New York, V.T. Lo, S.W. Lee.

Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.

Carus et al., "Initial Experience With The LigaSure™ Vessel Sealing System in Abdominal Surgery" Innovations That Work, Jun. 2002.

Chicharo et al., "A Sliding Goertzel Algorithm" Aug. 1996 DOS pp. 283-297 Signal Processing, Elsevier Science Publishers B.V. Amsterdam, NL, vol. 52, No. 3.

Chou, C.K., (1995) "Radiofrequency Hyperthermia in Cancer Therapy," Chapter 941n Biologic Effects of Nonionizing Electromagnetic Fields, CRC Press, Inc., pp. 1424-1428.

Chung et al., "Clinical Experience of Sutureless Closed Hemorrhoidectomy with LigaSure™" Diseases of the Colon & Rectum, vol. 46, No. 1, Jan. 2003.

Cosman et al., "Methods of Making Nervous System Lesions" In William RH, Rengachary SS (eds): Neurosurgery, New York: McGraw-Hill, vol. 111, (1984), pp. 2490-2499.

Cosman et al., "Radiofrequency Lesion Generation and its Effect on Tissue Impedence", Applied Neurophysiology, 51:230-242, 1988.

Cosman et al., "Theoretical Aspects of Radiofrequency Lesions in the Dorsal Root Entry Zone" Neurosurgery 15:(1984), pp. 945-950.

Crawford et al., "Use of the LigaSure™ Vessel Sealing System in Urologic Cancer Surger" Grand Rounds In Urology 1999, vol. 1, Issue 4, pp. 10-17.

Dulemba et al., "Use of a Bipolar Electrothermal Vessel Sealer in Laparoscopically Assisted Vaginal Hysterectomy" Sales/Product Literature; Jan. 2004.

E. David Crawford, "Evaluation of a New Vessel Sealing Device in Urologic Cancer Surgery" Sales/Product Literature 2000.

E. David Crawford, "Use of a Novel Vessel Sealing Technology in Management of the Dorsal Veinous Complex" Sales/Product Literature 2000.

Esterline, "Light Key Projection Keyboard" 2004 Advanced Input Systems, located at: <http://www.advanced-input.com/lightkey> last visited on Feb. 10, 2005.

Esterline Product Literature, "Light Key: Visualize a Virtual Keyboard. One With No Moving Parts", Nov. 1, 2003: 4 pages.

Geddes et al., "The Measurement of Physiologic Events by Electrical Impedence" Am. J. MI, Jan. Mar. 1964, pp. 16-27.

Goldberg et al., "Image-guided Radiofrequency Tumor Ablation: Challenges and Opportunities—Part 1", (2001) J Vasc. Interv. Radiol, vol. 12, pp. 1021-1032.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

Heniford et al., "Initial Results with an Electrothermal Bipolar Vessel Sealer" Surgical Endoscopy (2001) 15:799-801.

Herman et al., "Laparoscopic Intestinal Resection With the LigaSure™ Vessel Sealing System: A Case Report" Innovations That Work, Feb. 2002.

Humphries Jr. et al., "Finite-Element Codes to Model Electrical Heating and Non-Llnear Thermal Transport in Biological Media", Proc. ASME HTD-355, 131 (1997).

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Jarrett et al., "Use of the LigaSure™ Vessel Sealing System for Peri-Hilar Vessels in Laparoscopic Nephrectomy" Sales/Product Literature 2000.

Johnson et al., "Evaluation of a Bipolar Electrothermal Vessel Sealing Device in Hemorrhoidectomy" Sales/Product Literature, Jan. 2004.

Johnson, "Evaluation of the LigaSure™ Vessel Sealing System in Hemorrhoidectormy" American College of Surgeons (ACS) Clinic La Congress Poster (2000).

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General , Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, pp. 205-210.

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.

MDTech product literature (Dec. 1999) "FlexStrand": product description, 1 page.

MDTech product literature (Mar. 2000) I'D Wire: product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L. W., "Electrophysiologic Principles of Radiofrequency Lesion Making" Appl. Neurophysiol, vol. 39: pp. 69-76 (1976/1977).
P.R. Stauffer et al., "Interstitial Heating Technologies", Thermoradiotheray and Thermochemotherapy (1995) vol. 1, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (1 PEG) 2000.
Sayfan et al., "Sutureless Closed Hemorrhoidectomy: A New Technique" Annals of Surgery, vol. 234, No. I, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.

European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
European Search Report EP 10006373 dated Oct. 11, 2010.

* cited by examiner

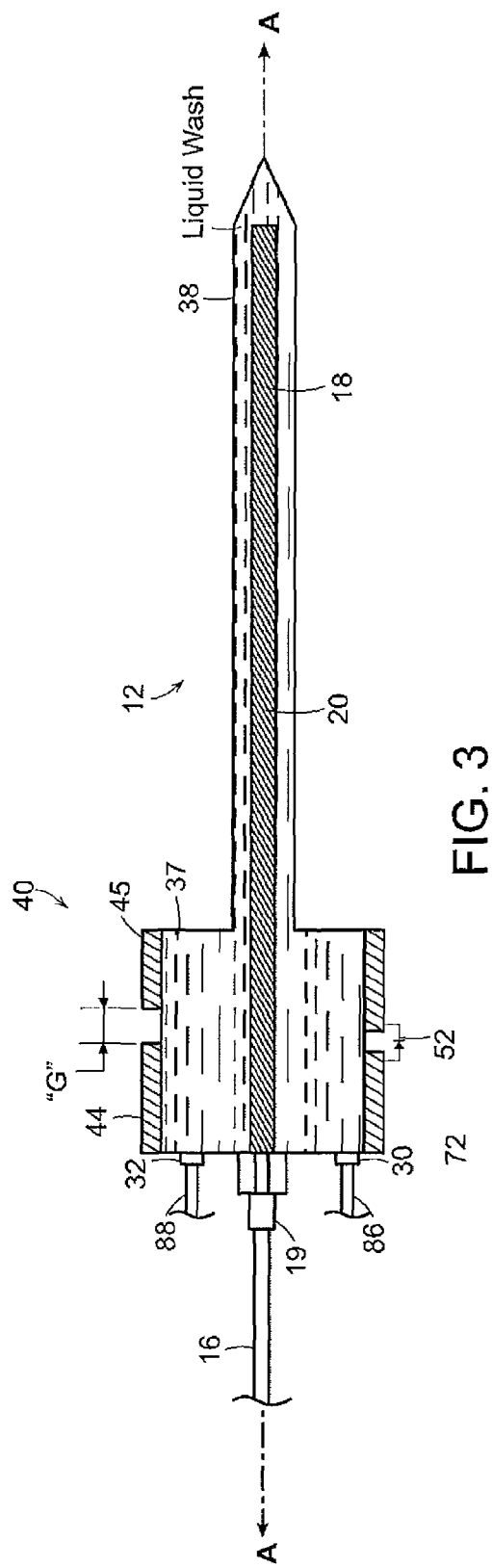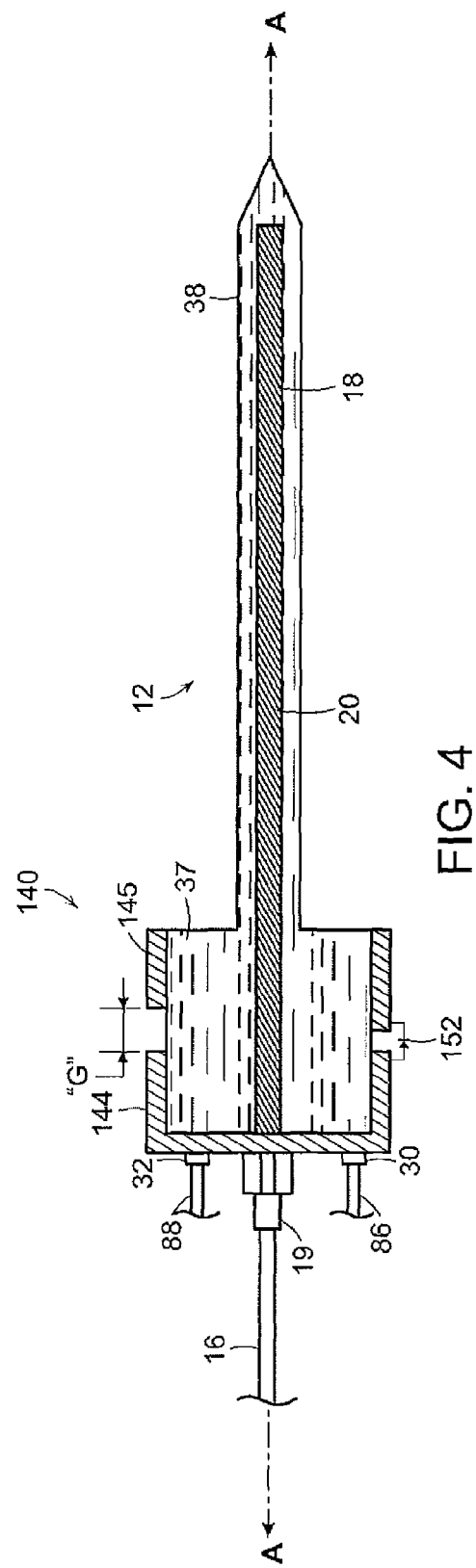

MICROWAVE ABLATION ANTENNA RADIATION DETECTOR

CROSS-REFERENCE TO RELATED APPLICATION

The present application is a continuation-in-part of a U.S. application Ser. No. 12/487,917 titled "Microwave Ablation Antenna Radiation Detector" by Joseph D. Brannan on Jun. 19, 2009, which is hereby incorporated by reference.

BACKGROUND

1. Technical Field

The present disclosure relates generally to microwave antennas. More particularly, the present disclosure is directed to radiation detectors for microwave ablation antennas.

2. Background of Related Art

Treatment of certain diseases requires destruction of malignant tissue growths (e.g., tumors). It is known that tumor cells denature at elevated temperatures that are slightly lower than temperatures injurious to surrounding healthy cells. Therefore, known treatment methods, such as hyperthermia therapy, heat tumor cells to temperatures above 41° C., while maintaining adjacent healthy cells at lower temperatures to avoid irreversible cell damage. Such methods involve applying electromagnetic radiation to heat tissue and include ablation and coagulation of tissue. In particular, microwave energy is used to coagulate and/or ablate tissue to denature or kill the cancerous cells.

Microwave energy is applied via microwave ablation antennas that penetrate tissue to reach tumors. There are several types of microwave antennas, such as monopole and dipole, in which microwave energy radiates perpendicularly from the axis of the conductor. A monopole antenna includes a single, elongated microwave conductor whereas a dipole antenna includes two conductors. In a dipole antenna, the conductors may be in a coaxial configuration including an inner conductor and an outer conductor separated by a dielectric portion. More specifically, dipole microwave antennas may have a long, thin inner conductor that extends along a longitudinal axis of the antenna and is surrounded by an outer conductor. In certain variations, a portion or portions of the outer conductor may be selectively removed to provide more effective outward radiation of energy. This type of microwave antenna construction is typically referred to as a "leaky waveguide" or "leaky coaxial" antenna.

Conventional microwave antennas operate at a single frequency allowing for creation of similarly shaped lesions (e.g., spherical, oblong, etc.). Some antennas are capable of radiating energy inside as well as outside tissue, due to well-tuned impedance matching. In some instances this may result in inadvertent radiation outside the tissue.

SUMMARY

According to one embodiment of the present disclosure, a radiation detector is disclosed. The radiation detector is disposed on a microwave antenna assembly. The radiation detector includes a receiving antenna adapted to receive microwave energy. The receiving antenna includes a first tubular antenna member and a second tubular antenna member disposed concentrically about a longitudinal axis defined by the microwave antenna assembly. The detector also includes at least one rectifier coupled to the receiving antenna adapted to rectify at least a portion of the microwave energy and a filter coupled to the at least one rectifier and adapted to convert the rectified microwave energy into a detection signal.

According to another embodiment of the present disclosure, a microwave antenna assembly is disclosed. The microwave antenna assembly includes a hub configured to couple the microwave antenna assembly to a microwave generator and a cooling system that circulates a coolant fluid through the antenna assembly. The microwave antenna assembly also includes a radiating section coupled to the hub through a feedline and a radiation detector disposed about the hub. The radiation detector includes a receiving antenna adapted to receive microwave energy. The receiving antenna includes a first tubular antenna member and a second tubular antenna member disposed concentrically about a longitudinal axis of the hub, the first and second tubular antenna members having with a predetermined gap defined therebetween. The receiving antenna also includes at least one rectifier coupled to the first and second tubular antenna members across the gap and adapted to rectify at least a portion of the microwave energy and a filter coupled to the at least one rectifier and adapted to convert the rectified microwave energy into a detection signal.

According to a further embodiment of the present disclosure, a microwave antenna assembly is disclosed. The microwave antenna assembly includes a hub configured to couple the microwave antenna assembly to a cable connector and a cooling system that circulates a coolant fluid through the antenna assembly. The microwave antenna assembly also includes a radiating section coupled to the hub through a feedline and a radiation detector disposed about the hub. The radiation detector includes a receiving antenna adapted to receive microwave energy. The receiving antenna includes a first tubular antenna member and a second tubular antenna member disposed concentrically about a longitudinal axis of the hub, the first and second tubular antenna members having a predetermined gap defined therebetween. The first tubular antenna member is coupled to the cable connector and the second tubular antenna member includes a hub portion and an extended portion extending over at least a portion of the radiating section. The receiving antenna also includes at least one rectifier coupled to the first and second tubular antenna members across the gap and adapted to rectify at least a portion of the microwave energy and a filter coupled to the at least one rectifier and adapted to convert the rectified microwave energy into a detection signal.

BRIEF DESCRIPTION OF THE DRAWINGS

The above and other aspects, features, and advantages of the present disclosure will become more apparent in light of the following detailed description when taken in conjunction with the accompanying drawings in which:

FIG. 3 is a sectional, side view of an antenna assembly according to one embodiment of the present disclosure;

FIG. 4 is a sectional, side view of an antenna assembly according to another embodiment of the present disclosure.

DETAILED DESCRIPTION

Particular embodiments of the present disclosure will be described herein below with reference to the accompanying drawings. In the following description, well-known functions or constructions are not described in detail to avoid obscuring the present disclosure in unnecessary detail.

The present disclosure provides for a radiation detector disposed on a microwave antenna. Generally, the detector is disposed in a location such that any unintended and/or errant radiation of microwave energy along the antenna is detected. The radiation detector converts the detected radiation into a detection signal, which is then transmitted to a control system (e.g., microwave generator) to either shut off the power supply and/or alert the user.

In one embodiment, the radiation detector includes a receiving antenna adapted to receive microwave energy radiating along the microwave antenna and a rectifying circuit including a rectifying device and a filter. The rectifying circuit rectifies the microwave energy incident on the receiving antenna into a sensing signal and then passes the sensing signal through the filter to the control system.

Figure 1:
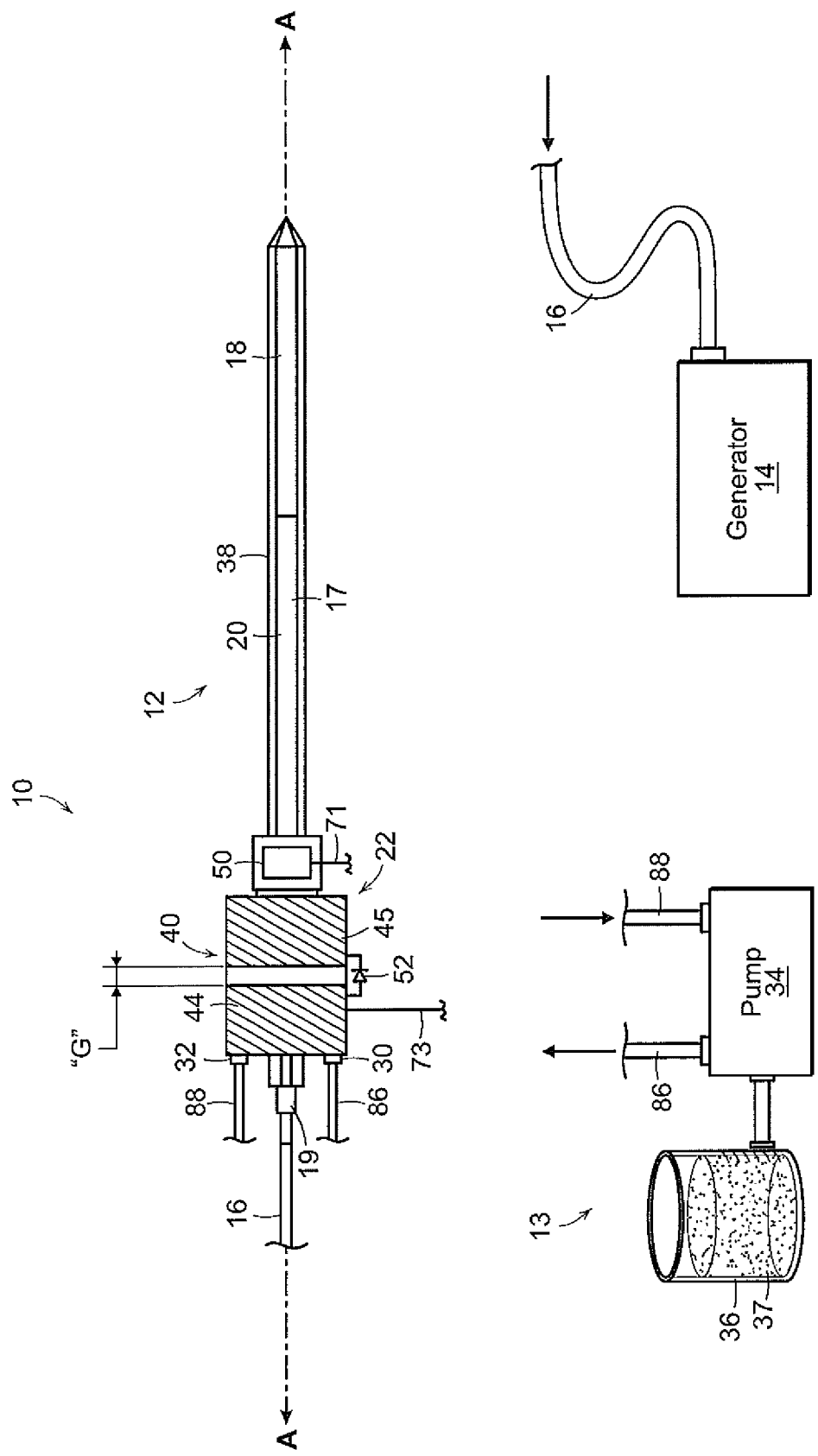
FIG. 1 is a schematic diagram of a microwave ablation system according to an embodiment of the present disclosure.

FIG. 1 shows a microwave ablation system 10 that includes a microwave antenna assembly 12 coupled to a microwave generator 14 via a flexible coaxial cable 16. The generator 14 is configured to provide microwave energy at an operational frequency from about 500 MHz to about 10,000 MHz. In the illustrated embodiment, the antenna assembly 12 includes a radiating section 18 connected by feedline 20 (or shaft) to the cable 16. More specifically, the feedline 20 is connected to a hub 22, which is connected to the cable 16 through a cable connector 19. The hub 22 may have a variety of suitable shapes, e.g., cylindrical, rectangular, etc.

The feedline 20 may be coaxial and may include an inner conductor surrounded by an inner insulator, which is, in turn, surrounded by an outer conductor 17 (e.g., a cylindrical conducting sheath). The outer conductor 17 is coupled to the outer conductor (not explicitly shown) of the cable 16 via the connector 19. The inner conductor and outer conductor 17 may be constructed of copper, gold, stainless steel or other conductive metals with similar conductivity values. The metals may be plated with other materials, e.g., other conductive materials, to improve their properties, e.g., to improve conductivity or decrease energy loss, etc. In one embodiment, the feedline 20 may be formed from a coaxial, semi-rigid or flexible cable having a wire with a 0.047" outer diameter rated for 50 Ohms.

The connection hub 22 also couples the antenna assembly 12 to a cooling system 13. The connection hub 22 includes an outlet fluid port 30 and an inlet fluid port 32 that are connected in fluid communication with a sheath 38. The sheath 38 encloses radiating portion 18 and feedline 20 allowing a coolant fluid 37 to circulate from ports 30 and 32 around the antenna assembly 12. The ports 30 and 32 are also coupled to a supply pump 34 that is, in turn, coupled to a supply tank 36 via supply lines 86 and 88, respectively. The supply pump 34 may be a peristaltic pump or any other suitable type. The supply tank 36 stores the coolant fluid 37 and, in one embodiment, may maintain the fluid at a predetermined temperature. More specifically, the supply tank 36 may include a coolant unit that cools the returning liquid from the antenna assembly 12. In another embodiment, the coolant fluid 37 may be a gas and/or a mixture of liquid and gas.

The coolant fluid 37 provides for dielectric impedance buffering for the antenna assembly 12. This allows for radiation of significant amounts of power while the antenna assembly 12 is partially inserted in the tissue or exposed to air. Although the buffering provides for increased coupling, errant radiation may leak from the antenna assembly 12. The antenna assembly 12 includes a radiation detector 40 disposed on the outer surface of the hub 22. The radiation detector 40 senses unintended radiation and shuts off the generator 14 if the sensed stray radiation exceeds predetermined safety thresholds. In another embodiment, the generator 14 may adjust the energy output therefrom in response to the sensed radiation.

With reference to FIGS. 1 and 3, the radiation detector 40 includes a cylindrical receiving antenna 42 formed as a first tubular antenna member 44 and a second tubular antenna member 45. The first antenna member 44 is disposed about a proximal portion of the hub 22 and the second antenna member 45 is disposed around a distal portion of the hub 22. As used herein the term "distal" refers to that portion of the antenna assembly 12, or component thereof, farther from the user while the term "proximal" refers to that portion of the antenna assembly 12 or component thereof, closer to the user.

The antenna members 44 and 45 are cylindrical tubes that are concentrically disposed on a top surface of the hub 22. In other words, the antenna members 44 and 45 are concentric to each other, such that the antenna members 44 and 45 are centered about a longitudinal axis A-A as defined by the antenna assembly 12.

In one embodiment, the hub 22 may be formed from a non-conductive, conformal material such as polyesters, polyimides, polyamides, polyamide-imides, polyetherimides, polyacrylates, polyethylene terephthalate, polyethylene, polypropylene, polyvinylidene chloride, polysiloxanes, combinations thereof and the like. The antenna and antenna members 44 and 45 may be formed from a conformal sheet of conductive material such as copper, gold, stainless steel or other conductive metals with similar conductivity values. In one embodiment, the receiving antenna 42 may be plated with other materials, e.g., other conductive materials, to improve, the conductive properties thereof. The radiation detector 40 may also be encased in an encasement shell (e.g., epoxy) to provide for sterilization compatibility. The encasement may be accomplished once the radiation detector 40 is conformed to the hub 22.

With reference to FIGS. 1 and 3, the antenna members 44 and 45 are separated by a gap distance "G." The radiation detector 40 also includes a rectifying circuit 50 coupled to one or more rectifiers 52 (FIG. 1) disposed across the gap "G." The rectifier 52 is electrically coupled to the antenna members 44 and 45. Rectifier 52 is placed in locations of high electric field density and low current density. The gap "G" may be arranged at any position along the hub 22. In other words, the antenna members 44 and 45 may be of varying width to optimized the voltage drop over the rectifier 52 based on the frequency of the microwave power being supplied to the antenna assembly 12.

The rectifier 52 may be any type of suitable diodes such as Zener diode, Schottky diode, tunnel diode and the like. The rectifier 52 may be in direct contact with the antenna members 44 and 45 or through an impedance matching network, which may include lumped elements and/or a transmission line. The rectifiers 52 convert the sinusoidal shape of the microwave waveform by clipping the negative portion of the waveform. In other words, the rectifiers 52 clip the bottom portion of the sinusoid to rectify the microwave waveform.

Figure 2B:
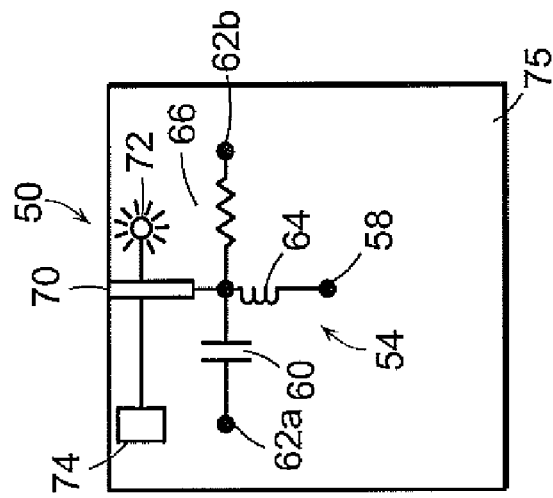
FIGS. 2A and 2B are schematic diagrams of rectifying circuits and a filter according to embodiments of the present disclosure.
Figure 2A:
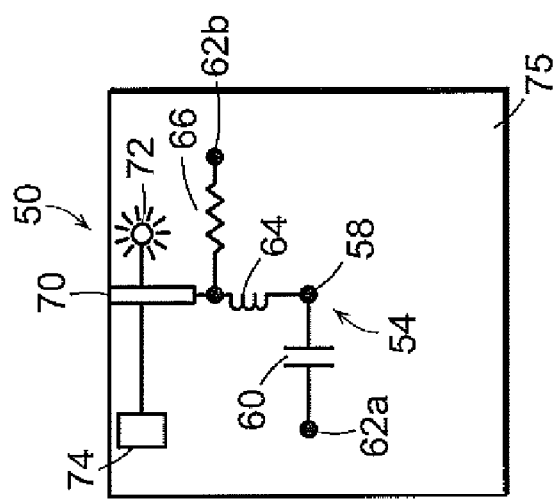

As shown in FIGS. 2A and B, rectifying circuit 50 includes a filter 54 that is coupled to the rectifier 52. The filter 54 may be an inductor-resistor-capacitor ("LRC") low pass filter that is adapted to convert the rectified sinusoidal waveform from the rectifiers 52 into a detection signal, which may be a DC voltage signal representative of the detected microwave radiation. The filter 54 is coupled to the rectifier 52 at connections 58, 62a, 62b. The connection 58 may be coupled to one terminal of the rectifier 52 and the connections 62a and 62b may be coupled to another terminal thereof.

The filter 54 includes a capacitor 60 coupled between the connections 58 and 62a. The capacitor 60 is connected in series with an inductor 64, which is connected through a resistor 66 to the connection 62b as shown in FIG. 2A. In another embodiment, the capacitor 60, the inductor 64 and the resistor 66 may be coupled to each other in parallel as shown in FIG. 2B. The inductor 64 is coupled to the receiving antenna at the connection 58.

The filter 54 is also connected to a voltage output 70 that may be coupled to a wire 71 (FIG. 1). The wire 71 may be disposed anywhere along the antenna assembly 12 such that the wire 71 has minimal effect on the radiation efficiency of the antenna assembly 12. When the filter 54 is configured as an LRC filter and connected to the voltage output 70, the filter 54 limits the microwave radiating from escaping through the wire 71 and allows the rectified DC current, namely, the detection signal to travel to the generator 14. A ground wire 73 is coupled to the antenna member 44 and provides the generator 14 with a reference signal for comparison of the detection signal therewith. The filter 54 also includes a high impedance voltage buffer 73 coupled to the voltage output 70. The voltage buffer 73 provides a reliable detection signal transmission to the generator 14.

The detection signal may then be transmitted to the generator 14 or another control system, which compares the detection signal with a reference threshold signal. The reference signal may be preset to denote a threshold level indicative of dangerous levels of microwave radiation. If the generator 14 determines that the detection signal is above the reference signal, then the generator 14 may terminate or suspend the supply of energy to the antenna assembly 12 and/or alert the user. The generator 14 may include any suitable type of alert or alarm (e.g., audio, visual, etc.) that is activated when the detection signal is above the threshold. In another embodiment, the generator 14 adjusts the output power as a function of the detection signal In other words, the generator 14 may lower or increase the output power based on the detected signal.

In another embodiment, in addition to transmission of the detection signal to the generator 14, the detection signal may also be used to power any suitable alarm device, such as a light-emitting device (e.g., LED 72) disposed on the bottom surface 41. The LED 72 may be configured to operate above a predetermined threshold voltage. This may be accomplished by coupling the LED 72 to a resistive divider network (not explicitly shown). Thus, the detection signals above the threshold trigger the LED 72, indicates to the user that dangerous levels of microwave energy are emitted outside the radiating section 18. In another embodiment, an audible alarm (e.g., a speaker) may be used in place of the LED 72.

In a further embodiment, the radiation detector 40 may include a voltage limiting circuit 74 to ensure that the voltage level of the detection signal is regulated, such that, excessive voltage does not pass to the control circuitry of the generator 14. The voltage limiting circuit 74 may include a Zener diode.

The rectifying circuit 50 and components thereof (e.g., filter 54) may be disposed on a dielectric substrate 75. In one embodiment, the rectifying circuit 50 may be formed as a printed circuit board, with the components thereof connected by traces on an epoxy resin substrate.

FIG. 4 illustrates another embodiment of a radiation detector 140 and includes a cylindrical receiving antenna 142 having a first antenna member 144 and a second antenna member 145. The first antenna member 144 is disposed about a proximal portion of the hub 22 and the second antenna member 145 is disposed around a distal portion of the hub 22. The antenna members 144 and 145 are cylindrical tubes that are concentrically disposed on a top surface of the hub 22. In other words, the antenna members 144 and 145 are concentric to each other, such that the antenna members 144 and 145 are centered about a longitudinal axis A-A as defined by the antenna assembly 12.

As discussed above with respect to FIGS. 1-3, the first and second antenna members 144 and 145 are also separated by a gap "G" and are coupled together by a rectifier 152. The rectifier 152 is, in turn, coupled to the rectifying circuit 50 (FIGS. 2A and 2B), which processes the detected microwave radiation.

In this embodiment, the first antenna member 144 is electrically coupled to the cable connector 19, more specifically to the outer conductor 17 to create a short-circuited coaxial geometry. This obviates the need for the ground wire 73 coupling the antenna member 144 to the generator 14. In other words, the coupling of the first antenna member 144 to the cable connector 19 provides the generator 14 with a reference signal for comparison of the detection signal from the rectifying circuit 50 therewith.

Figure 5:
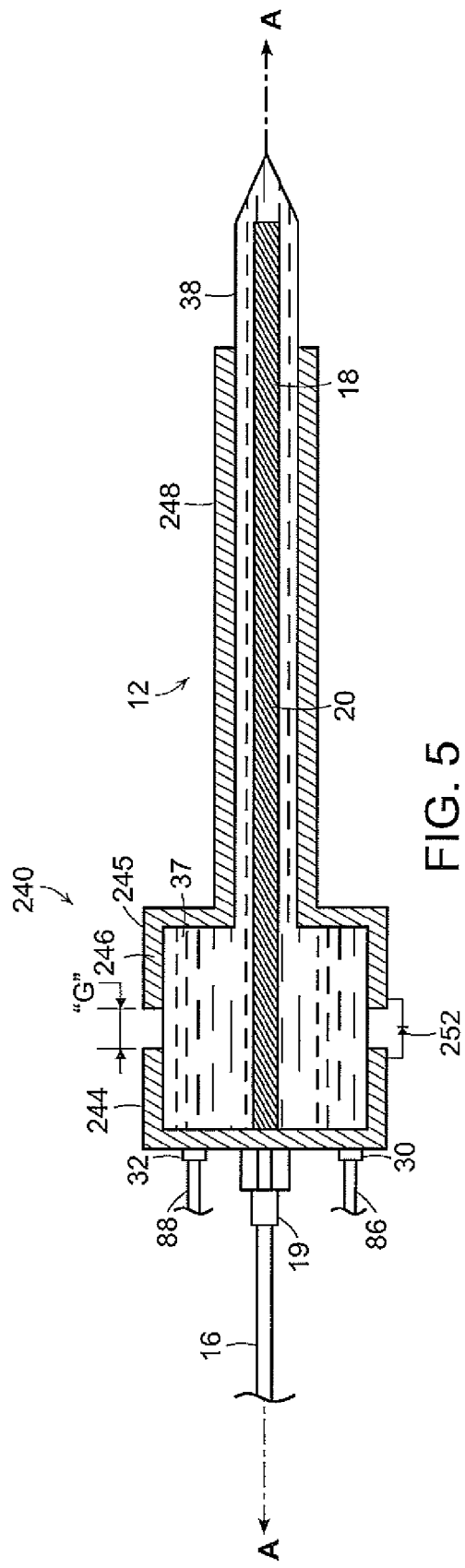
FIG. 5 is a sectional, side view of an antenna assembly according to another embodiment of the present disclosure.

FIG. 5 illustrates another embodiment of a radiation detector 240 that includes a cylindrical receiving antenna 242 having a first antenna member 244 and a second antenna member 245. The first antenna member 244 is disposed about a proximal portion of the hub 22 and the second antenna member 245 is disposed around a distal portion of the hub 22.

The antenna members 244 and 245 are cylindrical tubes that are concentrically disposed on a top surface of the hub 22. In other words, the antenna members 244 and 245 are concentric to each other, such that the antenna members 244 and 245 are centered about a longitudinal axis A-A as defined by the antenna assembly 12.

The second antenna member 245 includes a hub portion 246 and an extended portion 248 that extends distally along the feedline 20 up to a proximal end of the radiating section 18. The hub portion 246 is of substantially the same diameter as the first antenna member 244 and is disposed about the hub 22. The extended portion 248 may be of a smaller diameter than the hub portion 246 to better conform to a smaller diameter of the feedline 20.

Encasing of the hub 22 and the feedline 20 in the first and second antenna members 244 and 245 extends the effectiveness of the radiation detector 240, allowing for detection of stray microwave energy closer to the radiating section 18. This is particularly useful in laparoscopic or percutaneous applications, where tissue structures reside between the radiating section 18 and the hub 22 and it is useful to prevent damage to these structures.

As discussed above with respect to FIGS. 1-3, the first and second antenna members 244 and 245 are also separated by a gap "G" and are coupled together by a rectifier 252. The rectifier 252 is, in turn, coupled to the rectifying circuit 50 (FIGS. 2A and 2B), which processes the detection.

Similar to the embodiment of FIG. 4, the first antenna member 244 is electrically coupled to the cable connector 19, more specifically to the outer conductor 17 to create a short circuited coaxial geometry. This obviates the need for the ground wire 73 coupling the antenna member 244 to the generator 14. In other words, the coupling of the first antenna member 144 to the cable connector 19 provides the generator 14 with a reference signal for comparison of the detection signal from the rectifying circuit 50 therewith.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A radiation detector disposed on a microwave antenna assembly, the radiation detector comprising:
a receiving antenna adapted to receive microwave energy, the receiving antenna including a first tubular antenna member and a second tubular antenna member disposed concentrically about a longitudinal axis defined by the microwave antenna assembly, wherein the receiving antenna includes:
a hub configured to couple the microwave antenna assembly to a microwave generator; and
a cooling system that circulates a coolant fluid through the antenna assembly and wherein the first and second tubular antenna members are disposed about the hub;
at least one rectifier coupled to the receiving antenna adapted to rectify at least a portion of the microwave energy; and
a filter coupled to the at least one rectifier and adapted to convert the rectified microwave energy into a detection signal.

2. The radiation detector according to claim 1, wherein the hub is formed from a dielectric material and the first and second tubular antenna members are formed from a conductive material.

3. The radiation detector according to claim 1, wherein the first and second tubular antenna members are separated by a gap.

4. The radiation detector according to claim 1, wherein the least one rectifier is coupled to the first and second tubular antenna members across the gap.

5. The radiation detector according to claim 1, wherein the at least one rectifier is a diode.

6. The radiation detector according to claim 1, further comprising:
a light-emitting device coupled to the filter, the light-emitting device adapted to operate when the detection signal is above a predetermined threshold signal.

7. The radiation detector according to claim 1, wherein the filter includes a capacitor, an inductor and a resistor coupled in series or parallel.

8. The radiation detector according to claim 1, wherein first tubular antenna member is coupled to a cable connector.

9. The radiation detector according to claim 1, wherein the second tubular antenna member includes a hub portion having a first diameter and an extended portion having a second diameter smaller than the first diameter.

10. A microwave antenna assembly, comprising:
a hub configured to couple the microwave antenna assembly to a microwave generator and a cooling system that circulates a coolant fluid through the antenna assembly;
a radiating section coupled to the hub through a feedline; and
a radiation detector disposed about the hub, the radiation detector including:
a receiving antenna adapted to receive microwave energy, the receiving antenna including a first tubular antenna member and a second tubular antenna member disposed concentrically about a longitudinal axis of the hub, the first and second tubular antenna members having a predetermined gap defined therebetween;
at least one rectifier coupled to the first and second tubular antenna members across the gap and adapted to rectify at least a portion of the microwave energy; and
a filter coupled to the at least one rectifier and adapted to convert the rectified microwave energy into a detection signal.

11. The microwave antenna assembly according to claim 10, wherein the hub is formed from a dielectric material and the first and second tubular antenna members are formed from a conductive material.

12. The microwave antenna assembly according to claim 10, wherein the at least one rectifier is a diode.

13. The microwave antenna assembly according to claim 10, further comprising:
a light-emitting device coupled to the filter, the light-emitting device adapted to operate when the detection signal is above a predetermined threshold signal.

14. The microwave antenna assembly according to claim 10, wherein the filter includes a capacitor, an inductor and a resistor coupled in series or parallel.

15. The microwave antenna assembly according to claim 10, wherein first tubular antenna member is coupled to a cable connector.

16. The microwave antenna assembly according to claim 10, wherein the second tubular antenna member includes a hub portion having a first diameter and an extended portion having a second diameter smaller than the first diameter.

17. A microwave antenna assembly, comprising:
a hub configured to couple the microwave antenna assembly to a cable connector and a cooling system that circulates a coolant fluid through the antenna assembly;
a radiating section coupled to the hub through a feedline; and
a radiation detector disposed about the hub, the radiation detector comprising:
a receiving antenna adapted to receive microwave energy, the receiving antenna including a first tubular antenna member and a second tubular antenna member disposed concentrically about a longitudinal axis of the hub, the first and second tubular antenna members having a predetermined gap defined therebetween, wherein the first tubular antenna member is coupled to the cable connector and the second tubular antenna member includes a hub portion and an extended portion extending over at least a portion of the radiating section;
at least one rectifier coupled to the first and second tubular antenna members across the gap and adapted to rectify at least a portion of the microwave energy; and a filter coupled to the at least one rectifier and adapted to convert the rectified microwave energy into a detection signal.

18. The microwave antenna assembly according to claim 17, further comprising:
a light-emitting device coupled to the filter, the light-emitting device adapted to operate when the detection signal is above a predetermined threshold signal.

19. The microwave antenna assembly according to claim 17, wherein the filter includes a capacitor, an inductor and a resistor coupled in series or parallel.

20. A radiation detector disposed on a microwave antenna assembly, the radiation detector comprising:
a receiving antenna adapted to receive microwave energy, the receiving antenna including a first tubular antenna member and a second tubular antenna member disposed concentrically about a longitudinal axis defined by the microwave antenna assembly, wherein the first and second tubular antenna members are separated by a gap;

at least one rectifier coupled to the receiving antenna adapted to rectify at least a portion of the microwave energy, wherein the least one rectifier is coupled to the first and second tubular antenna members across the gap; and a filter coupled to the at least one rectifier and adapted to convert the rectified microwave energy into a detection signal.

21. A radiation detector disposed on a microwave antenna assembly, the radiation detector comprising:

a receiving antenna adapted to receive microwave energy, the receiving antenna including a first tubular antenna member and a second tubular antenna member disposed concentrically about a longitudinal axis defined by the microwave antenna assembly, wherein the second tubular antenna member includes a hub portion having a first diameter and an extended portion having a second diameter smaller than the first diameter;

at least one rectifier coupled to the receiving antenna adapted to rectify at least a portion of the microwave energy; and a filter coupled to the at least one rectifier and adapted to convert the rectified microwave energy into a detection signal.

\* \* \* \* \*